United States Patent [19]

Le Frock et al.

[11] 4,217,411
[45] Aug. 12, 1980

[54] NOVEL ENRICHMENTS FOR BLOOD CULTURE MEDIA

[76] Inventors: Jack L. Le Frock, 34 Woodstream Dr.; Ronald F. Schell, 41 Delmar Pl., both of Delmar, N.Y. 12054

[21] Appl. No.: 973,956

[22] Filed: Dec. 28, 1978

[51] Int. Cl.$^2$ .......................... C12Q 1/04; C12N 1/38; C12N 1/20; C12R 1/21
[52] U.S. Cl. ........................................ 435/34; 435/32; 435/244; 435/253; 435/851
[58] Field of Search .................... 435/34, 32, 244, 253, 435/254, 801, 851

[56] References Cited

U.S. PATENT DOCUMENTS

| | | | |
|---|---|---|---|
| 3,649,460 | 3/1972 | Controni et al. | 435/34 |
| 3,980,523 | 9/1976 | Rimler et al. | 435/253 X |

OTHER PUBLICATIONS

BBL Manual of Product and Laboratory Procedures, 5th Ed., Division of Becton, Dickinson and Company, pp. 160–161, 1973.
Edwin Lennette et al., Manual of Clinical Microbiology, 2nd Ed., American Society for Microbiology, p. 903, 1974.

*Primary Examiner*—Robert J. Warden
*Attorney, Agent, or Firm*—Cooper, Dunham, Clark, Griffin & Moran

[57] ABSTRACT

The present invention concerns novel enrichments for enhancing the detection of the etiological agents of bacteremia. The blood enrichments of this invention are based upon the discovery that a novel supplement which includes a Fildes peptic digest of blood and certain other compounds enables conventional blood culture media to support the growth of a greater variety of microorganisms than has been possible previously and to stimulate growth rates of microorganisms. Use of the enrichment of the present invention will permit prompt and accurate detection of a broad range of etiological agents of bacteremia and facilitate the work of clinical microbiologists. The products of the invention can be utilized in antibiotic sensitivity testing, and are especially useful in automated machines for such testing.

10 Claims, No Drawings

NOVEL ENRICHMENTS FOR BLOOD CULTURE MEDIA

The prompt and accurate isolation of the etiological agents of bacteremia is one of the most important functions performed by the clinical microbiology laboratory. It is important that the infecting organism or organisms be detected and identified rapidly in order for proper therapy to be provided promptly. However, there are a number of factors which adversely effect the isolation of bacteremic agents. One of the most significant of such factors is the blood culture medium used to support the growth of microorganisms present in clinical samples used in diagnostic testing.

Although it is estimated that there are more than 200 different commercially available blood culture media, there is no consensus among clinical microbiologists as to which of them is the most effective system for recovery of a wide variety of microorganisms, including aerobic, facultatively anaerobic and anaerobic microorganisms. To the contrary, there is no blood culture medium available which will support the growth of the entire spectrum of microorganisms encountered in the clinical laboratory. It has therefore been clear that there exists a need for developing an optimal blood culture medium which would permit rapid detection and identification of a broader range of etiological agents of bacteremia.

In accordance with the present invention, it has been found that blood culture media support the growth for a wide variety of microorganisms and permit early detection and identification of a broad range of etiological agents of bacteremia when a supplement of a Fildes peptic digest of blood and additional nutritional and growth-supporting compounds in amounts per 100 ml of the Fildes digest as follows is included in the media:

| | |
|---|---|
| Vitamin $B_{12}$ | 0.1–20 mg |
| Nicotinamide adenine dinucleotide | 10.0–40 mg |
| L-Glutamine | 100.0–2000 mg |
| Co-enzyme A | 0.1–80 mg |
| Pyruvate (Sodium) | 120.0–2500 mg |
| Catalase | 1.0–20 μg |
| Glutamate | 50.0–1000 mg |
| Vitamin $K_1$ | 10.0–500 μl |
| Co Carboxylase | 0.1–500 mg |
| Cysteine hydrochloride | 0.3–750 mg |

Additionally, vitamin $K_3$ and sodium metabisulfite in amounts from 0.1–500 mg and 0.01–10.0 mg, respectively, may be advantageously included in the supplement of this invention.

As mentioned previously, a wide variety of blood culture media are commercially available for use with aerobic, facultatively anaerobic and/or anaerobic microorganisms. However, no one of these commercial blood culture media is totally satisfactory for use across a broad spectrum of microorganisms.

In order to provide a blood culture medium capable of supporting a wider variety of microorganisms, a supplement may be added to the commercially available medium to increase its nutritional and growth-supporting capacity. Several such supplements are themselves commercially available including a Fildes digest from Baltimore Biological Laboratories, Isovitalex, also from Baltimore Biological Laboratories, and Hemin-vitamin K from Grand Island Biological Company.

As described more fully hereinafter, such supplements may be modified and improved utilizing the products of this invention.

EXPERIMENTAL PROCEDURE

All of the test results reported herein are based upon the following experimental procedure which includes comparisons of the enrichments of the invention with Fildes, Isovitalex and Hemin-Vitamin K.

Preparation of Enrichment

All blood culture media and supplements were purchased from commercial manufacturers. One, the enrichment, was prepared by us. This non-commercial Fildes digest was prepared by thoroughly mixing in a screwcap flask 150 milliliters of 0.85% NaCl, 6 milliliters of concentrated HCl, 50 milliliters of defibrinated sheep blood, and 1 g of granular pepsin. The mixture was then placed in a 55° C. water bath, shaken occasionally during the first 2 hours and then left in the water bath overnight. After 16 to 18 hours at 55° C., about 6 ml of 5 N.NaOH was added until the pH was 7.0 or slightly less. The digested blood was supplemented with chemicals as indicated below, centrifuged, filtered, sterilized and aseptically divided into convenient aliquots in sterile bottles or tubes and stored for subsequent use. Before such use, the peptic digest was warmed gently and added to the sterilized blood culture medium in an amount from about 1–10 ml, e.g. 1.5 ml, of peptic digest per 98.5 ml of medium.

Blood culture bottles contained approximately 50 ml of medium with either sodium polyethanol sulfonate or sodium amylosulfate in amounts ranging from 0.025–0.03 percent by weight.

Microorganisms

The aerobic or facultatively anaerobic microorganisms were chosen to represent those frequently isolated from bacteremic individuals or those having fastidious growth requirements. Seed cultures were prepared by inoculating brain heart infusion (BHI) broth with a single colony obtained from a recent clinical isolate. Separate 100 ml aliquots of BHI broth were inoculated with individual seed cultures. CVA (co-enzyme, vitamins and amino-acids) enrichment obtained from Grand Island Biological Company was added to the BHI broth to facilitate the growth of microorganisms. After incubation at 35° C. for 18 hours, the cultures were centrifuged at 10,000 rpm for 20 minutes. The pellets were resuspended and washed three times with fresh BHI broth. After the final centrifugation, the pellets were resuspended in 20 mls of BHI broth and 2 ml aliquots of each microorganism were placed in vials, sealed, and stored in liquid nitrogen.

The anaerobic microorganisms were chosen to represent those commonly isolated from bacteremic individuals or those which required a low oxidation-reduction potential ($E_h$). Seed cultures were prepared by inoculating BHI broth supplemented with 1% Hemin-vitamin K with a single colony obtained from recent clinical isolates (blood, pleural fluid, wounds, etc.) The cultures were incubated at 35° C. for 18 hours in an anaerobic glove box. After incubation, the cultures were centrifuged and resuspended in fresh pre-reduced BHI broth containing 15% glycerol. 2 ml aliquots were placed in vials, sealed, and stored in liquid nitrogen.

Determination of the number of microorganisms used for innoculation of blood culture media In order to simulate low-grade bacteremia, an inoculum of less than twenty microorganisms was introduced into the blood culture bottles. Frozen vials containing the microorganisms were thawed and the bacterial suspensions were serially diluted to yield final concentrations of 8–20 microorganisms per ml. The actual number of microorganisms introduced into each blood culture medium was determined by plating an aliquot (0.5 ml) of the inoculum on pre-reduced blood agar plates and/or chocolate agar plates. Colonies were counted 24–48 hours after incubation at 35° C. and the number of organisms per ml of inoculum was determined.

Preparation of human serum and erythrocytes

A single lot of pooled human serum was used. Healthy volunteers who were not on antibiotic therapy during the preceding two weeks served as blood donors. The serum was separated by centrifugation at 2,000 rpm for 15 minutes, sterilized by membrane filtration (0.22 μm pore size) and stored at −70° C. until use to prevent the inactivation of complement. Group "O" erythrocytes were obtained from the hospital blood bank approximately two days after donation and washed three times with saline. The serum and erythrocytes were tested for sterility.

Inoculation of blood culture bottles

Blood culture bottle stoppers were cleansed with 70% alcohol, disinfected with Betadine for one minute and washed with 70% alcohol. One ml of BHI broth, or in the case of the anaerobic microorganisms pre-reduced BHI broth, containing a selected dilution of microorganisms was injected into duplicate blood culture bottles with or without the red blood cell-serum mixture (RBC-SM). The RBC-SM contained 2.25 ml erythrocytes and 2.75 ml of serum. The bottles were agitated, incubated at 35° C. and subcultured for various periods of time after inoculation. Subculturing was performed in the case of aerobic and facultatively anaerobic microorganisms by inoculating chocolate agar plates and in the case of anaerobic microorganisms pre-reduced blood agar plates with 0.1 ml of blood culture medium. Plates were examined for bacterial growth at various times after inoculation, and after a predetermined time, the microorganisms were recovered and the recovery rate determined.

In order to provide a blood culture medium having the capacity to support a broader range of microorganisms, three commercially available supplements referred to hereinabove, namely, Fildes digest, Isovitalex, and Hemin-vitamin K were compared to determine their effect on the growth of *Haemophilus influenzae* organisms when added to brain heart infusion broth medium, both alone and in the presence of red blood cell-serum mixture. Without an additional supplement, brain heart infusion broth blood culture medium would not support the growth of *Haemophilus influenzae*. The results of this comparison are shown in Tables I, II and III.

TABLE I

Concentration effect of supplements[1] on the growth of Haemophilus influenzae type b organisms[2]

| Supplement | \multicolumn{9}{c}{Final concentration of supplement} | | | | | | | | |
|---|---|---|---|---|---|---|---|---|---|
| | 1:2 | 1:4 | 1:8 | 1:16 | 1:32 | 1:64 | 1:128 | $1:10^3$ | $1:10^4$ |
| FILDES (commercial) | $NG^3$ | NG | NG | NG | NG | $1 \times 10^{9*}$ | $1 \times 10^9$ | $2 \times 10^8$ | NG |
| ISOVITALEX | $NG^3$ | NG | NG | NG | NG | $4 \times 10^5$ | $6 \times 10^9$ | NG | NG |
| HEMIN-VITAMIN K | NG | NG | NG | NG | NG | NG | NG | NG | NG |

[1] Supplements were added to BHI broth
[2] Cultures were inoculated with 10 (CFU) organisms
[3] No growth of the microorganisms was observed in 18 hours after inoculation
*CFU/ml 18 hours after inoculation

TABLE II

Concentration effect of supplements[1] on the growth of Haemophilus influenzae type b organisms[2] in the presence of red blood cell-serum mixture

| Supplement | 1:2 | 1:4 | 1:8 | 1:16 | 1:32 | 1:64 | 1:128 | $1:10^3$ | $1:10^4$ |
|---|---|---|---|---|---|---|---|---|---|
| FILDES (commercial) | $NG^3$ | $7.5 \times 10^{8*}$ | $9 \times 10^8$ | $1.5 \times 10^9$ | $9.5 \times 10^8$ | $3 \times 10^9$ | $3.2 \times 10^9$ | $1.5 \times 10^8$ | $1 \times 10^6$ |
| ISOVITALEX | NG | NG | NG | $2.5 \times 10^9$ | $2.5 \times 10^9$ | $6 \times 10^8$ | $4 \times 10^8$ | $7.5 \times 10^7$ | $2.5 \times 10^6$ |
| HEMIN-VITAMIN K | NG | NG | $1.3 \times 10^6$ | $2.5 \times 10^6$ | $2 \times 10^6$ | $4 \times 10^6$ | $1 \times 10^6$ | $1.7 \times 10^6$ | NG |

[1] Supplements were added to BHI broth
[2] Cultures were inoculated with 10 (CFU) organisms
[3] No growth of the microorganisms was observed in 18 hours after inoculation
*CFU/ml 18 hours after inoculation

TABLE III

Growth of various strains of Haemophilus influenzae in BHI broth supplemented with Fildes or Isovitalex 18 hours after inoculation

| Haemophilus influenzae | Inoculum size | Concentration of Fildes | | | Concentration of Isovitalex | | |
|---|---|---|---|---|---|---|---|
| | | 1:32 | 1:64 | 1:128 | 1:32 | 1:64 | 1:128 |
| type b | 10 | $NG^1$ | $1 \times 10^9$ | $1 \times 10^9$ | NG | $4 \times 10^5$ | $6 \times 10^5$ |
| type c | 12 | $1.5 \times 10^9$ | $1 \times 10^9$ | $3 \times 10^8$ | $1.5 \times 10^5$ | $1 \times 10^6$ | $2 \times 10^5$ |
| type d | 15 | $4 \times 10^7$ | $1 \times 10^8$ | $6 \times 10^7$ | NG | $5 \times 10^3$ | $1 \times 10^4$ |

From Table I it can be seen that after addition of the commercial Fildes digest supplement, the medium supported growth of *Haemophilus influenzae* type b at concentrations from about 0.1-2.0 percent, and moreover that the Fildes supplement was more effective than the other commercial supplements examined. In the presence of red blood cell-serum mixture, the commercial Fildes supplement was even more effective. As Table II indicates the Fildes digest supplement supported growth at concentrations from 0.01-25.0 percent, with the maximum support being from about 0.5-2.0 percent. Finally, the Fildes supplement alone was compared with Isovitalex in terms of yielding colony forming units (CFU) per ml for other *Haemophilus influenzae* strains, namely, types b, c and d. Table III shows that the Fildes supplement continued to be more effective than Isovitalex. A Fildes concentration from about 0.5-2.0 percent, particularly about 1.5 percent, was most effective.

Based upon these results, commercial Fildes digest supplement was tested at a concentration of about 1.5 percent in brain heart infusion broth blood culture medium to determine its effect on the growth of a variety of aerobic, facultatively anaerobic, and anaerobic microorganisms. The results of this test are shown in Table IV, and indicate that although commercial Fildes digest supplement is effective in supporting the growth of *Haemophilus influenzae* and other fastidious microorganisms, the supplement does not support the growth of a number of other organisms including *Streptococcus pneumoniae*, *Bacteroides melaninogenicus*, *Actinomyces Israelii*, *Neisseria gonorrhoeae*, *Peptostreptococcus anaerobius*, and *Veilonella parvula*.

TABLE IV

Influence of 1.5 per cent concentration of Commercial Fildes and modified Fildes enrichment in BHI broth on growth of aerobic, facultatively anaerobic and anaerobic microorganisms 18 hours after inoculation

| Microorganisms | Inoculum size | Commercial Fildes CFU/ml | Modified Fildes CFU/ml |
|---|---|---|---|
| *Acinetobacter calcoaceticus* var. lwoffi | 5 | $1.85 \times 10^6$ | $4 \times 10^8$ |
| *Escherichia coli* | 3 | $5 \times 10^8$ | $3.5 \times 10^9$ |
| *Listeria monocytogenes* | 27 | $1 \times 10^7$ | $2 \times 10^9$ |
| *Neisseria gonorrhoeae* | 12 | NG[1] | $4 \times 10^9$ |
| *N. meningitidis* | 8 | NG | $3.5 \times 10^8$ |
| *Staphylococcus aureus* | 10 | $2 \times 10^7$ | $2 \times 10^9$ |
| *Streptococcus pneumoniae* (clinical isolate #1) | 18 | NG | $1.85 \times 10^8$ |
| *S. pneumoniae* (clinical isolate #2) | 14 | $8 \times 0\,10^8$ | |
| *S. pneumoniae* (clinical isolate #3) | 16 | NG | $9 \times 10^7$ |
| *S. pyogenes* | 14 | $7.5 \times 10^5$ | $1 \times 10^9$ |
| *Candida albicans* | 6 | $6 \times 10^5$ | $8.5 \times 10^8$ |
| *Actinomyces israelii* | 20 | NG | $8 \times 10^7$ |
| *Bacteroides fragilis* | 15 | $5 \times 10^6$ | $7.5 \times 10^8$ |
| *B. melaninogenicus* | 13 | NG | $9 \times 10^7$ |
| *Cloatridium novyll* | 9 | $1 \times 10^4$ | $5 \times 10^8$ |
| *Fusobacterium necrophorus* | 14 | $2 \times 10^5$ | $1 \times 10^8$ |
| *Peptostreptococcus anaerobius* | 11 | NG | $2.5 \times 10^8$ |
| *Propionibacterium acnes* | 9 | $1 \times 10^5$ | $2 \times 10^9$ |
| *Veilonella parvula* | 15 | NG | $1.85 \times 10^8$ |

[1]No growth of the microorganisms was observed 18 hours after inoculation.

In order to overcome the inhibitory effects of commercial Fildes on the growth of certain microorganisms, a modified Fildes enrichment was prepared. Additional compounds in amounts per liter of Fildes digest were added as follows:

| | |
|---|---|
| Vitamin $B_{12}$ | 100 μg |
| Nicotinamide adenine dinucleotide | 250 μg |
| L-Glutamine | 10,000 μg |
| Co-enzyme A | 100 μg |
| Pyruvate (sodium) | 10,000 μg |
| Catalase | 50 μg |
| Glutamate | 5,000 μg |
| Vitamin $K_1$ | 1,000 μl |
| Co-Carboxylase | 200 μg |
| Cysteine hydrochloride | 100 μg* |

*10 μg/μl - final concentration in blood culture medium.

The effect of the modified Fildes enrichment on the growth of a variety of microorganisms is also shown in Table IV. From this table it is clear that the modified Fildes enrichment prepared in accordance with this invention is effective in augmenting the growth of a broad range of aerobic, facultatively anaerobic, and anaerobic microorganisms.

In order to determine whether the modified Fildes enrichment of the present invention was effective when included in other blood culture media, a series of experiments were conducted involving the growth of fastidious microorganisms and anaerobic microroganisms on various blood culture media. The percentage of microorganisms recovered from the blood culture media are shown in Tables V and VI.

TABLE V

PERCENTAGE OF FASTIDIOUS MICROORGANISMS RECOVERED FROM BLOOD CULTURE MEDIA

| | WITHOUT MODIFIED FILDES | | WITH MODIFIED FILDES | |
|---|---|---|---|---|
| MEDIUM | DAY 1 | DAY 4 | DAY 1 | DAY 4 |
| Brucella broth[1] | 0 | 0 | 80 | 100 |
| Columbia broth[1] | 25 | 50 | 80 | 80 |
| Dextrose Phosphate broth[2] | 50 | 100 | 100 | 100 |
| Trypticase soy broth[3] | 50 | 50 | 100 | 100 |
| Brain heart infusion broth[3] | 50 | 75 | 100 | 100 |
| Supplemented peptone broth[4] | 25 | 25 | 60 | 80 |
| Trypticase soy broth[4] | 50 | 75 | 80 | 80 |
| Lederle blood culture media[5] | 25 | 50 | 100 | 100 |

[1]Pfizer Diagnostics, New York City
[2]Grand Island Biological Company, Madison, Wisconsin
[3]Baltimore Biological Laboratories, Corkville, Maryland
[4]Becton-Dickinson, Silver Springs, Maryland
[5]Lederle Diagnostics, Pearl River, New York

TABLE VI

PERCENTAGE OF ANAEROBIC MICROORGANISMS RECOVERED FROM ANAEROBIC BLOOD CULTURE MEDIA

| | WITHOUT MODIFIED FILDES | | WITH MODIFIED FILDES | |
|---|---|---|---|---|
| MEDIUM | DAY 1 | DAY 4 | DAY 1 | DAY 4 |
| Lederle blood culture medium[1] | 25 | 62 | 40 | 85 |
| Thioglycollate medium[2] | 50 | 50 | 88 | 100 |
| Thioglycollate medium[3] | 37 | 75 | 50 | 57 |
| Thioglycollate medium[4] | 12 | 37 | 50 | 57 |
| Thioglycollate medium[5] | 12 | 25 | 63 | 63 |
| Thiol broth[3] | 50 | 37 | 75 | 85 |

[1]Lederle Diagnostics
[2]Becton-Dickinson
[3]Difco, Detroit, Michigan
[4]Pfizer Diagnostics
[5]Baltimore Biological Laboratories These results clearly indicate that the modified Fildes enrichment of the present invention is effective in increasing the recovery of a wide variety of microorganisms when used in conjunction with numerous commercially available blood culture media.

It is thus possible to rapidly and accurately detect numerous etiological agents of bacteremia by incorporating the modified Fildes enrichment of this invention in blood culture media which has been inoculated with a clinical sample such as a blood, pleural fluid, or like samples obtained from a patient. After incubating the inoculated media to facilitate growth of microorganisms which are present in the sample, it is possible to isolate and identify the microorganism or microorganisms present using conventional techniques.

As will be obvious to one skilled in the art, many modifications, variations, and/or substitutions can be made in the practices of the present invention without departing from the spirit and scope thereof as set forth in the claims which follow.

We claim:

1. An enrichment for blood culture media which comprises Fildes and additional compounds in amounts per 100 ml of Fildes as follows:

| | |
|---|---|
| Vitamin $B_{12}$ | 0.1–20 mg |
| Nicotinamide adenine dinucleotide | 10.0–40 mg |
| L-Glutamine | 100.0–2000 mg |
| Co-enzyme A | 0.1–80 mg |
| Pyruvate (Sodium) | 120.0–2500 mg |
| Catalase | 1.0–20 μg |
| Glutamate | 50.0–1000 mg |
| Vitamin $K_1$ | 10.0–500 μl |
| Co Carboxylase | 0.1–500 mg |
| Cysteine hydrochloride | 0.3–750 mg |

2. The enrichment of claim 1 which additionally comprises vitamin $K_3$ in an amount from 0.1–500 mg and sodium metabisulfite in an amount from 0.01–10.0 mg.

3. A blood culture medium which contains the enrichment of claim 2.

4. A blood culture medium in accordance with claim 3 which additionally comprises a serum-red blood cell mixture.

5. A blood culture medium in accordance with claim 3 wherein said enrichment is present in said blood culture medium in a concentration of from about 0.1 to 10.0 percent by weight.

6. A method of detecting etiological agents of bacteremia which comprises inoculating the blood culture medium of claim 3 with a sample drawn from a subject, incubating the innoculated medium for a sufficient period of time to support the growth of microorganisms present in said sample on said culture medium and identifying said microorganisms.

7. A blood culture medium which contains the enrichment of claim 1.

8. A blood culture medium in accordance with claim 7 which additionally comprises a serum-red blood cell mixture.

9. A blood culture medium in accordance with claim 7 wherein said enrichment is present in said blood culture medium in a concentration of from about 0.1 to 10.0 percent by weight.

10. A method of detecting etiological agents of bacteremia which comprises inoculating the blood culture medium of claim 7 with a sample drawn from a subject, incubating the innoculated medium for a sufficient period of time to support the growth of microorganisms present in said sample on said culture medium and identifying said microorganisms.

* * * * *